United States Patent [19]

Baker et al.

[11] 4,001,427
[45] Jan. 4, 1977

[54] N-DIMETHYLACETONITRILE-α-(SUBSTITUTED PHENOXY) ALKYLAMIDES AND THEIR USE AS MITICIDES

[75] Inventors: Don R. Baker, Orinda; Francis H. Walker, Mill Valley, both of Calif.

[73] Assignee: Stauffer Chemical Company, Westport, Conn.

[22] Filed: June 30, 1975

[21] Appl. No.: 591,727

[52] U.S. Cl. .......................... 424/304; 260/465 D
[51] Int. Cl.² .................. A01N 9/20; A01N 9/24; C07C 121/78
[58] Field of Search ............... 260/465 D; 424/304

[56] References Cited
UNITED STATES PATENTS 3,557,209   1/1971   Richter et al. ............... 260/465 D Primary Examiner—V. D. Turner
Attorney, Agent, or Firm—Michael J. Bradley

[57] ABSTRACT

Miticidally active compounds, defined by the generic formula

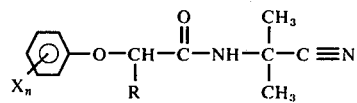

wherein R is either methyl or ethyl, X is either chlorine or trifluoromethyl, and n is either 1 or 3, are described herein.

26 Claims, No Drawings

N-DIMETHYLACETONITRILE-α-(SUBSTITUTED PHENOXY) ALKYLAMIDES AND THEIR USE AS MITICIDES

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat. No. 2,426,885 and its two continuations-in-part, U.S. Pat. Nos. 2,484,295 and 2,484,296. Herbicidal properties of such compounds are taught in U.S. Pats. Nos. 3,272,844, 3,439,018 and 3,564,607, and Belgian Pat. No. 739,714.

BRIEF DESCRIPTION OF THE INVENTION

This invention relates to a class of substituted amides and to their use as miticides when used in a miticidally effective amount. More specifically, this invention relates to N-dimethylacetonitrilo-α-(substituted phenoxy) alkylamides having the formula

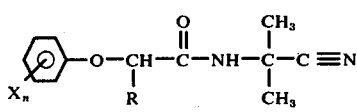

wherein R is either methyl or ethyl, and X is either chlorine or trifluoromethyl, and where X is chlorine, $n$ is 3 with the proviso that the 2- and 4-positions are not both occupied on the phenyl ring; and where X is trifluoromethyl, $n$ is 1.

By "miticidally effective amount" is meant the amount of the herein disclosed miticidal compounds which when applied to the habitat of mites in any conventional manner will kill or substantially injure a significant portion of the population thereon.

DETAILED DESCRIPTION OF THE INVENTION

The compounds of the present invention are prepared by the following general method:

Reaction No. 1

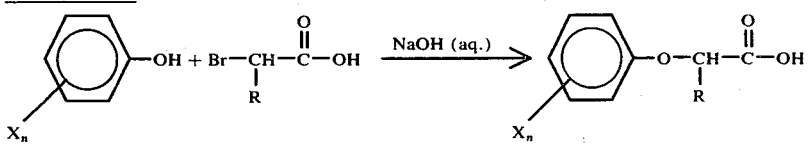

A slight molar excess of 50% aqueous NaOH is added to a mixture of a molar amount of the phenol and a slight molar excess of the acid. Water, perchloroethylene, and concentrated HCl are then added and the product acid is recovered from the organic phase.

Reaction No. 2

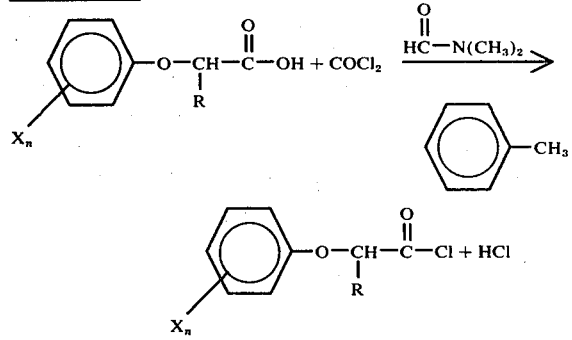

A slight molar excess of phosgene is introduced into a slurry of a molar amount of the acid in toluene, to which a small amount of dimethyl formamide has been added. The solution is purged to remove the excess phosgene and HCl, and the solvent is evaporated to leave the acid chloride.

Reaction No. 3

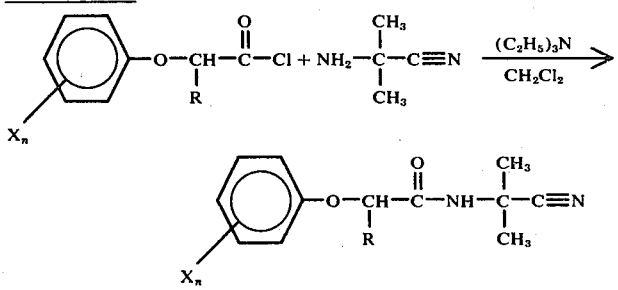

The acid chloride is added to a dichloromethane solution of both α-aminoisobutyronile and triethylamine at 10°–15° C. After successive washings with water, dilute HCl, and Na₂CO₃ solution, the product is recovered from the organic phase.

The examples shown herein are illustrative of the method of preparation of the compounds of the invention.

EXAMPLE I

N-dimethylacetonitrilo-α-(3,4,5-trichlorophenoxy)-butyramide.

(Compound No. 1 in Table I below)

50.8 g (0.63 mole) of 50% aqueous sodium hydroxide was added to a mixture of 50 g (0.25 mole) of 3,4,5-trichlorophenol and 50 g (0.30 mole) of 2-bromobutyric acid, with rapid stirring at an initial temperature of 15° C. The temperature rose to 45° C over the course of the addition and was held between 15° C and 45° C with a cold bath. At the completion of the sodium hydroxide addition, the cold bath was removed and the mixture was heated to 110° C for 15 minutes. Then 62 ml water, 125 ml perchloroethylene, and 50 ml concentrated hydrochloric acid were added to the reaction mixture. The mixture was heated to 85° C, then phase-separated. The organic layer was cooled and the product, α-(3,4,5-trichlorophenoxy)butyric acid, crystallized. The acid was separated by filtration and amounted to 54.2 g (76% yield), m.p. 115°–118° C.

0.2 ml dimethyl formamide was added to a slurry of 54.2 g (0.19 mole) of α-(3,4,5-trichlorophenoxy)-butyric acid in 75 ml toluene. The slurry was then heated to 60° C in a 500 ml flask fitted with a gas-inlet tube, a stirrer, a thermometer and a dry ice-isopropyl alcohol condenser. 22 g (0.23 mole of phosgene was passed into the mixture at a moderate rate. The dry ice condenser was then removed and replaced with a watercooled condenser. Excess phosgene and HCl were removed as the solution was purged with argon at 60° C. The solution was then cooled, and the solvent was removed in vacuum to leave 54.9 g (95.6% yield) of a liquid, $n_D^{30}$ 1.5506, which was α-(3,4,5-trichlorophenoxy)butyryl chloride.

8.0 g (0.03 mole) of the acid chloride was added dropwise to a mixture of 2.5 g (0.03 mole) of α-aminoisobutyronitrile [made by the procedure of J. V. Dubsky and W. D. Wensink, Ber. 49, 1136 (1916)] and 3.1 g (0.03 mole) of triethylamine in 100 ml methylene chloride at 10°–15° C. An ice bath was used to maintain the temperature. After the addition of the acid chloride, the mixture was allowed to come to room temperature and the product was isolated by washing with, in succession, 100 ml portions of water, dilute HCl, 5% Na₂CO₃ solution and water. The organic phase was dried over magnesium sulfate and the solvent was removed in vacuum to give 5.6 g (48.7% yield) of the product, identified by infrared spectroscopy as N-dimethylacetonitrilo-α-(3,4,5-trichlorophenoxy)butyramide, m.p. 162°–164° C.

EXAMPLE II

N-dimethylacetonitrilo-α-(2,3,5-trichlorophenoxy)-butyramide (Compound No. 2 in Table I below)

44.0 g (0.55 mole) of 50% aqueous sodium hydroxide was added to a mixture of 42.5 g (0.22 mole) of 2,3,5-trichlorophenol and 43.4 g (0.26 mole) of 2-bromobutyric acid, with rapid stirring at an initial temperature of 15° C. The temperature rose to 45° C over the course of the addition during which time a cold water bath was applied. At the completion of the sodium hydroxide addition, the cold bath was removed and the mixture was heated to 110° C for a 15-minute period. Then 50 ml of water, 53 ml of perchloroethylene, and 42 ml of concentrated hydrochloric acid were added and the mixture was heated to 85° C, then phase-separated. The organic layer was cooled and the product, α-(2,3,5-trichlorophenoxy)butyric acid, crystallized. The acid was isolated by filtration to give 43.1 g (69.1% yield) of α-(2,3,5-trichlorophenoxy)butyric acid, m.p. 106°–114° C.

0.2 ml of dimethyl formamide was added to a slurry of 50.3 g (0.18 mole) of α-(2,3,5-trichlorophenoxy)-butyric acid in 80 ml of toluene. The slurry was then heated to 60° C in a 500 ml flask fitted with a gas-inlet tube, a stirrer, a thermometer, and a dry ice-isopropyl alcohol condenser. 22 g (0.23 mole) of phosgene was passed into the mixture at a moderate rate. The dry ice condenser was then removed and replaced with the water-cooled condenser. Excess phosgene and HCl were removed by an argon purge of the solution at 60° C. The solution was then cooled, and the solvent was removed in vacuum to leave 43.4 g (80% yield) of an oil, which was α-(2,3,5-trichlorophenoxy)butyryl chloride.

8.0 g (0.03 mole) of the acid chloride was added dropwise to a mixture of 2.9 g (0.04 mole) of α-aminoisobutyronitrile and 3.7 g (0.04 mole) of triethylamine in 100 ml methylene chloride, maintained at a temperature of 10°–15° C by an ice bath. After the addition of the acid chloride, the mixture was allowed to come to room temperature and the product was isolated by washing with, in succession, 100 ml portions of water, dilute HCl, 5% Na₂CO₃ solution and water. The organic phase was dried over magnesium sulfate and the solvent was removed in vacuum to leave 7.8 g (74.4% yield) of N-dimethylacetonitrilo-α-(2,3,5-trichlorophenoxy)butyramide, m.p. 137°–140° C, characterized by infrared spectroscopy.

Other compounds, such as those included in the following table, can be prepared in a manner analogous to that shown in the examples above, starting with the appropriate materials. The compounds in the table are representative of those embodied in the present invention. Compound numbers have been assigned to them for purposes of identification throughout the balance of the specification.

TABLE I

| COMPOUND NUMBER | COMPOUND | MELTING POINT |
| --- | --- | --- |
| 1 | 2,4,5-trichlorophenyl-O-CH(C$_2$H$_5$)-C(O)-NH-C(CH$_3$)$_2$-C≡N | 162–164° C |
| 2 | 2,4,6-trichlorophenyl-O-CH(C$_2$H$_5$)-C(O)-NH-C(CH$_3$)$_2$-C≡N | 137–140° C |
| 3 | 2-CF$_3$-phenyl-O-CH(C$_2$H$_5$)-C(O)-NH-C(CH$_3$)$_2$-C≡N | 72–75° C |
| 4 | 2,4,5-trichlorophenyl-O-CH(CH$_3$)-C(O)-NH-C(CH$_3$)$_2$-C≡N | 133–136° C |
| 5 | 2,4,6-trichlorophenyl-O-CH(CH$_3$)-C(O)-NH-C(CH$_3$)$_2$-C≡N | 136–140° C |

Miticidal activity of each of the above compounds on the two-spotted mite [*Tetranychus urticae* (Koch)] was evaluated as follows:

I. Plant Dip Assay

Pinto bean plants (*Phaseolus sp.*), approximately 10 cm tall, are transplanted into sandy loam soil in 3-inch clay pots and thoroughly infested with two-spotted mites of mixed ages and sexes. Twenty-four hours later the infested plants are inverted and dipped for 2–3 seconds in 50-50 acetone-water solutions of the test chemicals. Treated plants are held in the greenhouse, and seven days later mortality is determined for both the adult mites and the nymphs hatching from eggs which were on the plants at the time of treatment. Test concentrations range from 0.2% down to that at which 50% mortality occurs (LD-50).

II. Systemic Assay

Test chemicals are dissolved in acetone and aliquots are diluted in 200 cc of water in glass bottles. Two pinto bean plants (*Phaseolus sp.*), with expanded primary leaves, are supported in each bottle by cotton plugs, so that their roots and stems are immersed in the treated water. The plants are then infested with 75–100 two-spotted mites of various ages and sexes. One week later the mortality of the adult mites and nymphs is recorded. Test concentrations range from 10 ppm down to that at which 50% mortality occurs (LD-50).

The following is a table of the results of the above test procedures, indicating the effective concentration at which LD-50 control effect was achieved.

TABLE II

Effective Concentrations on Two-Spotted Mite [*Tetranychus urticae* (Koch)]

| COMPOUND NUMBER | PE (%) | Eggs (%) | SYS (ppm) |
| --- | --- | --- | --- |
| 1 | .008 | .01 | >10 |
| 2 | .005 | >.05 | 10 |
| 3 | .03 | .05 | >10 |
| 4 | .005 | .03 | >10 |
| 5 | >.2 | .15 | — |

PE = Post-embryonic
SYS = Systemic
> = Greater than

Neither the examples nor the tables hereinabove are intended to limit the invention in any manner.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in miticide preparations. One such composition can contain either a single miticidally active compound or a combination of miticidally active compounds. The miticide compositions of this invention can contain as adjuvants organic solvents such as sesame oil, xylene, or heavy petroleum; water; emulsifying agents; surface active agents; talc; pyrophyllite; diatomite, gypsum;

clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence, such as light, or by some physiological action which the compound induces when it is ingested into the body of the pest.

The precise manner in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

We claim:

1. A compound having the formula

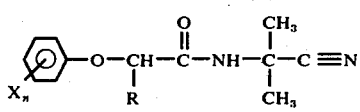

wherein R is either methyl or ethyl; X is either chlorine or trifluoromethyl; and where X is chlorine, $n$ is 3 with the proviso that the 2- and 4-positions are not both occupied on the phenyl ring; and where X is trifluoromethyl, $n$ is 1.

2. A compound according to claim 1 in which X is chlorine.
3. A compound according to claim 1 in which R is methyl.
4. A compound according to claim 1 in which X is chlorine and R is methyl.
5. A compound according to claim 4 in which the chlorine atoms occupy the 3-, 4-, and 5-positions on the phenyl ring.
6. A compound according to claim 4 in which the chlorine atoms occupy the 2-, 3-, and 5-positions on the phenyl ring.
7. A compound according to claim 1 in which R is ethyl.
8. A compound according to claim 1 in which X is chlorine and R is ethyl.
9. A compound according to claim 8 in which the chlorine atoms occupy the 3-, 4-, and 5-positions on the phenyl ring.
10. A compound according to claim 8 in which the chlorine atoms occupy the 2-, 3-, and 5-positions on the phenyl ring.
11. A compound according to claim 1 in which X is trifluoromethyl.
12. A compound according to claim 1 in which X is trifluoromethyl and R is ethyl.
13. A compound according to claim 12 in which X is 3-trifluoromethyl.
14. A method of controlling mites comprising applying to said mites a miticidally effective amount of a compound having the formula

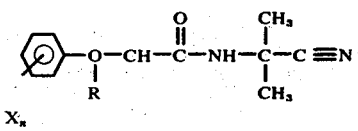

wherein R is either methyl or ethyl; X is either chlorine or trifluoromethyl; and where X is chlorine, $n$ is 3 with the proviso that the 2- and 4-positions are not both occupied on the phenyl ring; and where X is trifluoromethyl, $n$ is 1.

15. A method according to claim 14 in which X is chlorine.
16. A method according to claim 14 in which R is methyl.
17. A method according to claim 14 in which X is chlorine and R is methyl.
18. A method according to claim 17 in which the chlorine atoms occupy the 3-, 4-, and 5-positions on the phenyl ring.
19. A method according to claim 17 in which the chlorine atoms occupy the 2-, 3-, and 5-positions on the phenyl ring.
20. A method according to claim 14 in which R is ethyl.
21. A method according to claim 14 in which X is chlorine and R is ethyl.
22. A method according to claim 21 in which the chlorine atoms occupy the 3-, 4-, and 5-positions on the phenyl ring.
23. A method according to claim 21 in which the chlorine atoms occupy the 2-, 3-, and 5-positions on the phenyl ring.
24. A method according to claim 14 in which X is trifluoromethyl.
25. A method according to claim 14 in which X is trifluoromethyl and R is ethyl.
26. A method according to claim 25 in which X is 3-trifluoromethyl.

* * * * *